United States Patent [19]

Greene

[11] Patent Number: 5,704,946
[45] Date of Patent: Jan. 6, 1998

[54] MULTI-PURPOSE PROSTHETIC KNEE COMPONENT

[75] Inventor: Ted J. Greene, La Canada, Calif.

[73] Assignee: United States Manufacturing Company, Pasadena, Calif.

[21] Appl. No.: 614,646

[22] Filed: Mar. 13, 1996

[51] Int. Cl.⁶ ........................................... A61F 2/38
[52] U.S. Cl. ..................................... 623/44; 623/39
[58] Field of Search ............................... 623/39–47

[56] References Cited

U.S. PATENT DOCUMENTS

| 2,452,459 | 10/1948 | Hanger, III | 623/46 |
| 4,065,815 | 1/1978 | Sen-Jung | 623/40 |
| 5,376,137 | 12/1994 | Shorter et al. | 623/44 |
| 5,383,939 | 1/1995 | James | 623/44 |

FOREIGN PATENT DOCUMENTS

| 56602 | 7/1982 | European Pat. Off. | 623/44 |
| 1109153 | 8/1984 | U.S.S.R. | 623/44 |
| 2161386 | 1/1986 | United Kingdom | 623/44 |
| 2203347 | 10/1988 | United Kingdom | 623/39 |

Primary Examiner—John G. Weiss
Assistant Examiner—Bruce E. Snow
Attorney, Agent, or Firm—Christie, Parker & Hale, LLP

[57] ABSTRACT

A prosthetic knee component for an above knee prosthesis having a frame member and a bracket member pivotally connected to the frame member, thereby creating a center of rotation for the knee component. The knee component further including a gait control unit pivotally positioned between the frame member and the bracket member by flanges extending from a rear portion of the bracket member. A flexion bumper is positioned through the frame member away from the center of rotation and is sufficiently compressible in a flexion phase of the knee component to provide controlled energy absorbing compliance under force exerted on the bumper by the rear flanges. The knee component further includes an optional running gait flexion limiter positioned on an interior surface of the frame member for limiting flexion and providing inertia to the lower leg component during a running gait. The running gait flexion limiter provides inertia to the lower leg component by being sufficiently resilient in a flexion phase of the knee component to provide a controlled spring rate to the flanges on the bracket member to quickly return the lower leg component to an extension phase.

16 Claims, 4 Drawing Sheets

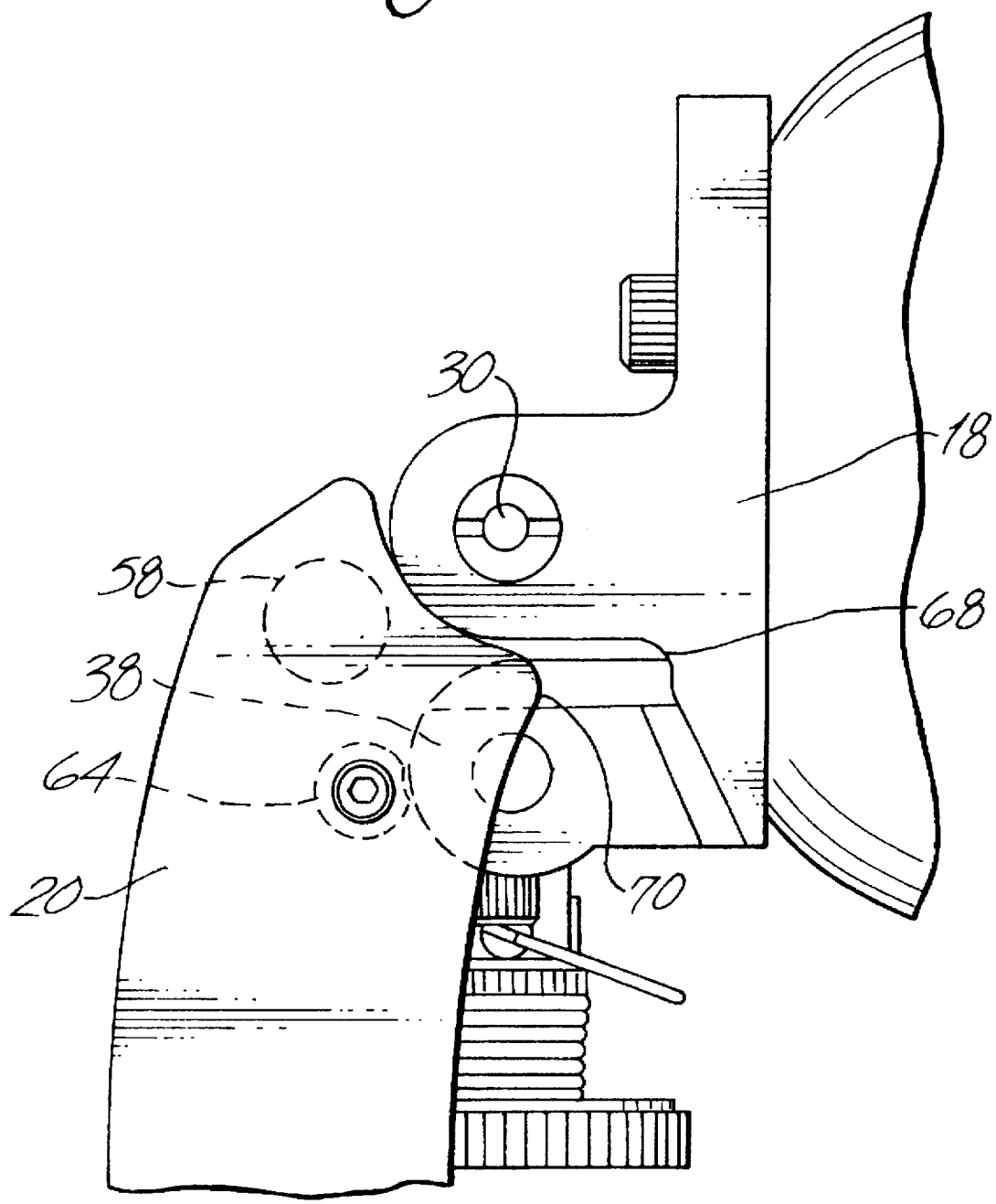

MULTI-PURPOSE PROSTHETIC KNEE COMPONENT

This invention relates generally to prosthetic devices, and more particularly to a prosthetic knee component designed for use with heavy or very active individuals. The knee component includes a flexion bumper and/or a running gait control positioned on the frame of the knee component away from the center of rotation of the knee so that the flexion bumper absorbs energy and the running gait control provides inertia to a lower leg component.

BACKGROUND OF THE INVENTION

Various types of foot and leg prosthetic devices are well known in the art. Such devices generally include some form of attachment for coupling the device to the distal end of the limb and for extending to the ground to provide body support. One form of prosthetic device is fabricated as an assembly having an upper leg component, a knee component, a lower leg component, and a foot component. The knee component provides rotation between the upper leg and the lower leg components.

Some currently available knee components utilized in above-knee prostheses consist of a knee bracket pivotally connected to a frame member by a main shaft and further connected to the frame member by a piston-type gait control unit. Typical gait control units are either hydraulic, pneumatic, or mechanical cylinders.

The knee component operates by rigidly attaching the knee bracket to a thigh component of the prosthesis and rigidly connecting the frame to the lower leg component. The gait control unit controls the movement of the frame with respect to the knee bracket during knee flexion and extension.

A problem with currently available prosthetic knee components is that the frame and the knee bracket are often constructed of metal, usually aluminum, and during maximum knee flexion the frame and the bracket come into contact, causing potential damage to either the knee bracket or the frame. This problem is most prevalent with heavy and very active individuals when heavy impact occurs. The force exerted on the knee bracket by heavy or very active individuals reduces the useful life of the prosthetic knee component and produces the undesirable, expensive, and inconvenient result of early wear and replacement of the prosthetic knee component.

Another significant problem with currently available prosthetic knee components is that they are not well suited for running. This problem is particularly faced by athletic amputees who compete competitively. A limiting factor for a sprinter caused by a prosthesis is the time required to return the knee component from the flexion phase to the extension phase. The frame of the knee component impacts the knee bracket during each stride before returning to extension; this increases the time required to complete a running stride. Currently available knee components have been designed for walking and have not been designed to quickly return the knee component to the full extension position which would enhance the performance of a runner.

Consequently, there exists a need for a new and improved prosthetic knee component designed to withstand rigorous use placed on it by heavy or active amputees, while also being capable of enhancing the performance of a runner.

SUMMARY OF THE INVENTION

The present invention provides a prosthetic knee component for above-knee prostheses which eliminates the problems of prior existing prosthetic knee components by providing a prolonged useful life, and improving the performance of athletes.

In one embodiment of the invention, the knee component comprises a bracket member pivotally connected to a frame member by a main shaft. The center of rotation of the knee component is about the main shaft. The frame member is rotated between flexion and extension with respect to the bracket member by the amputee's residual limb musculature. A control unit rigidly connected between the bracket member and the frame member dampens the movement between them and provides a reasonably symmetrical gait. The control unit is rigidly connected to the bracket member by a pin passing through ear segments extending downwardly from a rear portion of the bracket. The knee component is designed to withstand the large forces placed on the component by incorporating a flexion bumper spaced away from the center of rotation to compliantly absorb the forces generated between the bracket member and the frame member at the point of full flexion contact. A bore is located in the upper front corner of the frame portion to receive the flexion bumper which comes into contact with the downwardly extending ear segments on the bracket member and absorbs energy during knee flexion. The flexion bumper is made from an elastomeric material with adjustable densities to absorb enough of the force generated during knee flexion to either eliminate the metal-to-metal contact between the frame member and the bracket member during full flexion, or to reduce the force sufficiently so that no damage is done to the bracket member and the frame member when they come into contact.

The flexion bumper is retained within the frame member and is removable by end plugs which allows the use of different density bumpers to control the level of energy absorbed during knee flexion as desired by the user. The flexion bumper is specifically positioned in the upper front corner of the frame member so that the energy is absorbed away from the center of rotation between the bracket member and the frame member. Absorbing energy away from the center of rotation allows the bumper to absorb a greater amount of force than if positioned near the center of rotation. The flexion bumper's location also reduces the stress between the bracket member and the frame member at the center of rotation.

The knee component also enhances the performance of runners by including optional running gait flexion limiters on the frame member. A second bore is positioned below and inward from the flexion bumper bore in either side of the frame member for the attachment of the running gait limiters. The running gait limiters comprise an elastomeric or rigid material secured to the inside of the frame by a fastener passing through the bore. During running the downwardly extending ear portions of the bracket member come into contact with the gait limiters which initially absorbs the energy and quickly returns the frame member to the extension phase by producing an opposite spring force. The gait limiters act as a bumper to limit knee flexion to less than 90° and to absorb energy during knee flexion and as a spring to transfer inertia to the frame member during knee extension. A runner's performance is enhanced by the faster transition from knee flexion to extension since the angular movement in each direction is severely limited. As with the flexion bumpers, the running gait limiters are removable, and a variety of densities and sizes of the bumper material can be incorporated to control spring force and energy absorption and to change the amount of flexion angle to thereby accommodate the specific requirements of the individual user.

BRIEF DESCRIPTION OF THE DRAWINGS

FIG. 4 is a side elevational view of the knee component of FIG. 2 illustrating compression of the running gait control during the flexion phase.

DETAILED DESCRIPTION

Figure 1:
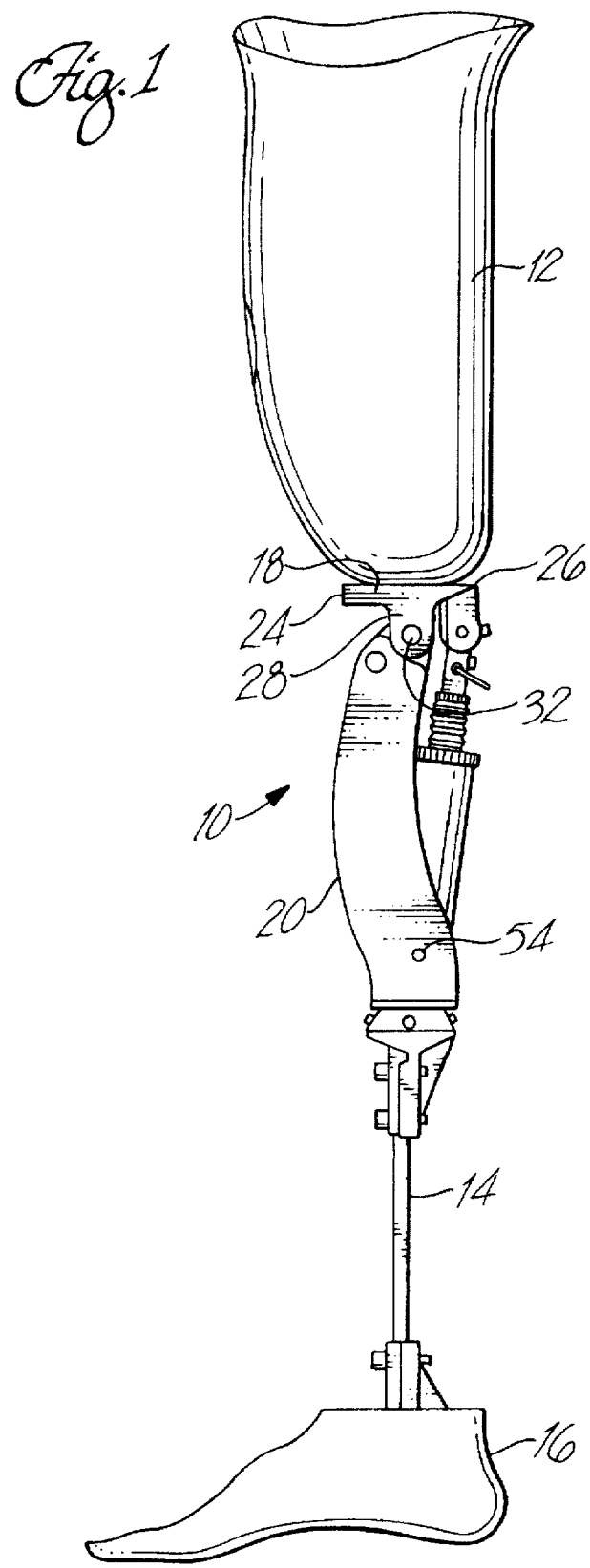
FIG. 1 is a side elevational view of the multi-purpose prosthetic knee component of the present invention incorporated into an above-knee prosthesis.
Figure 2:
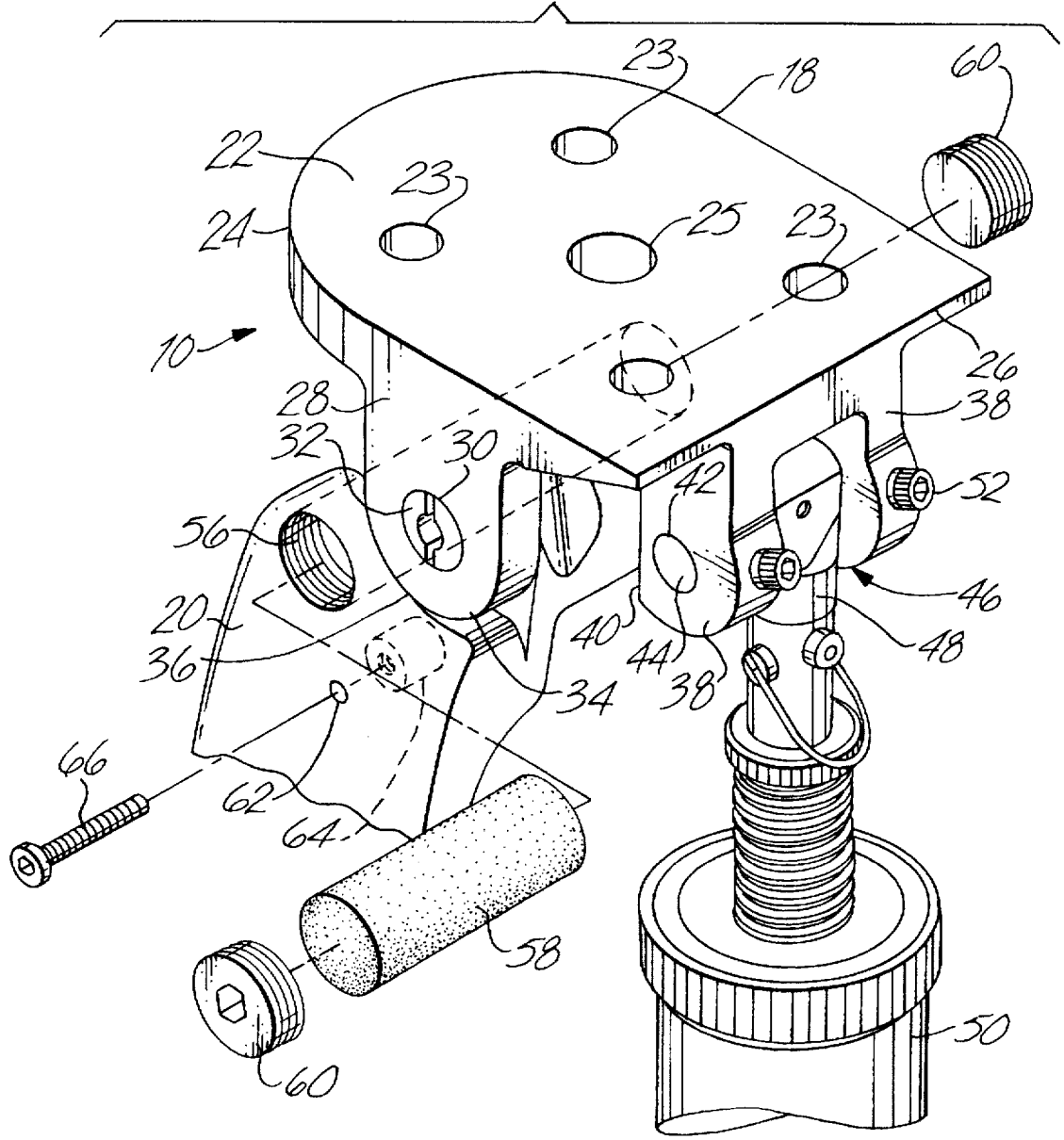
FIG. 2 is a partially exploded perspective view of the knee component of FIG. 1.

FIGS. 1 and 2 illustrate the multi-purpose prosthetic knee component 10 of the present invention. The knee component is positioned between a thigh component 12 and a lower leg component 14. A foot component 16 is connected to the lower end of lower leg component 14. Thigh, knee, lower leg, and foot components all comprise what is commonly known as an above-knee prosthesis.

The knee component simulates flexion between the thigh component 12 and the lower leg component 14. As seen best in FIG. 2 the knee component comprises a bracket member 18 pivotally connected to the top of a frame member 20. Bracket member 18 includes a generally flat base having an upper surface 22 with a curved front portion 24 and a straight back portion 26. Upper surface 22 includes a standard pattern of holes 23, and a larger centrally located hole 25, either of which can be utilized to attach the thigh component. A separate flange 28 extends downwardly along each side of the bracket member. Each flange 28 includes a bore 30 which receives a main shaft 32 which also passes through a bore in either side of the frame member 20 for pivotally connecting bracket member 18 to frame member 20. Main shaft 32 defines a central axis of rotation between bracket member 18 and frame member 20. Flange 28 includes a curved lower surface 34 which rotates adjacent a curved upper surface 36 of frame member 20 during flexion of the knee component.

Bracket member 18 includes two ears 38 extending downwardly from back portion 26. Ears 38 include a straight front surface 40 and a curved lower surface 41. Ears 38 also include a bore 42 for receiving a pin 44. Ears 38 define a cavity 46 for receiving a cylinder rod 48 of control unit 50. Control unit 50 is shown as a hydraulic cylinder, however pneumatic or mechanical control units can also be used. Piston rod 48 is held in position in cavity 46 and rotatably connected to ears 38 by pin 44. Pin 44 is positioned in ears 38 by set screws 52. As seen in FIG. 1, the opposite end of the control unit is rotatably attached to frame 20 by pin 54.

An internally threaded bore 56 is positioned in the upper front corner of frame 20 and passes through to the opposite side of the frame member for receiving a cylindrical flexion bumper 58. Flexion bumper is a solid cylindrical tube made of an elastomeric material such as gum rubber, silicone rubber, polyurethane, neoprene, or the like. The flexion bumper can be resiliently compressed by a lateral force applied to it during use to absorb the energy of the applied force. The density of the flexion bumper can be varied to absorb the forces exerted on the bumper and to suit the individual user's preference. The flexion bumper is held within bore 56 by externally threaded plugs 60. Plugs 60 also can be tightened by the user to squeeze against the ends of the flexion bumper to adjust the rate at which the flexion forces are absorbed.

A smaller threaded bore 62 is positioned in either side of the frame member 20, below and slightly rearwardly from bore 56, for attachment of an optional running gait flexion limiter 64. Flexion limiter 64 is preferably a cylindrical member made from a hard rigid material such as metal. The flexion limiter 64 is held along the inside surface of frame 20 by bolt 66, which passes through the hole 62 and threads into a central threaded passage in the flexion limiter. It is to be understood that although only one flexion limiter assembly is shown, a similar flexion limiter of the same size, shape and material is attached to the inside surface of frame 20 opposite from limiter 64, such that there are two flexion limiters aligned on a common axis and serving the identical function.

Figure 3:
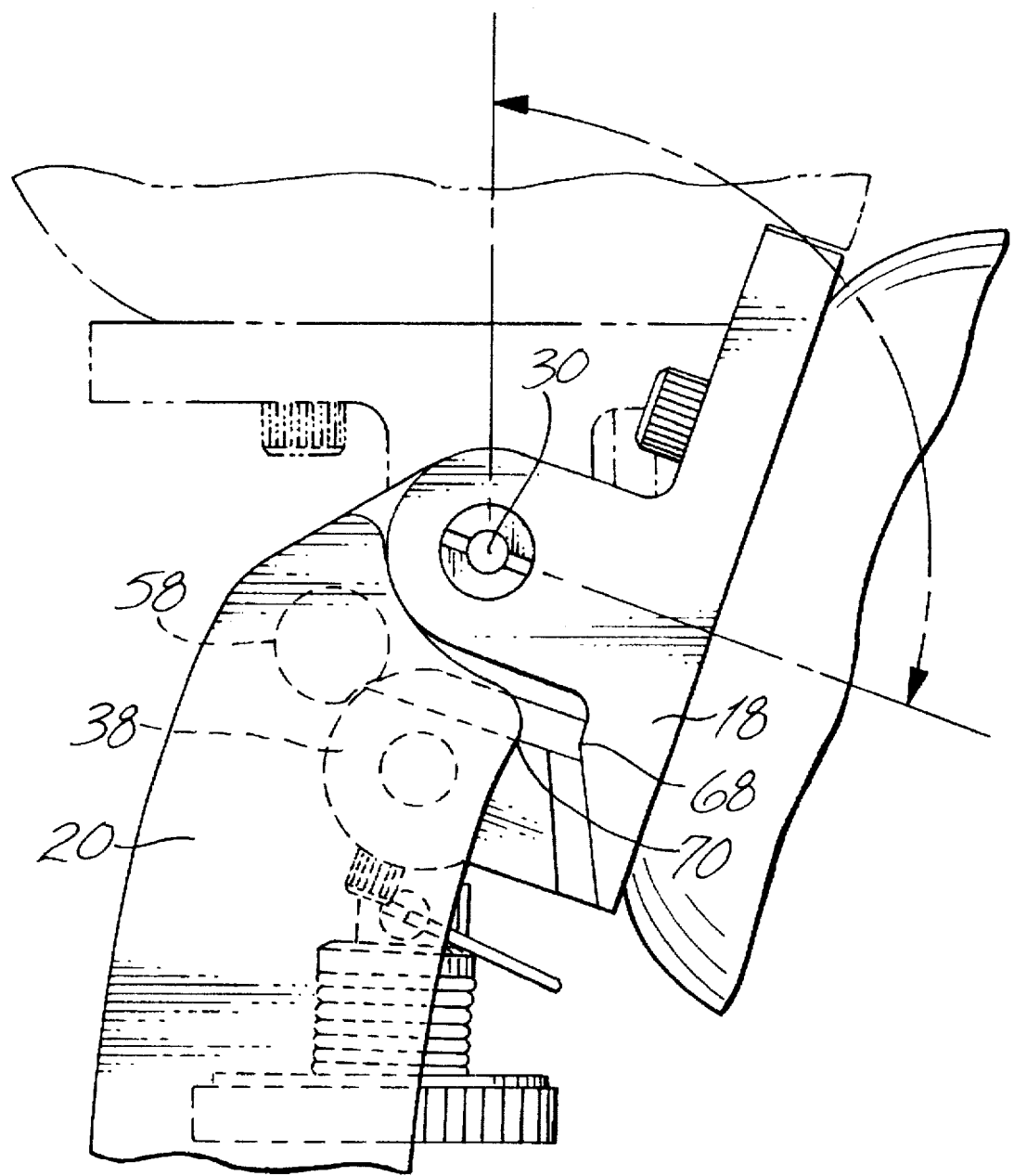
FIG. 3 is a side elevational view of the knee component of FIG. 2 illustrating compression of the flexion bumper during flexion phase.

Referring to FIG. 3, operation of the flexion bumper 58 is shown. Normally, without the flexion bumper, bracket member 18 in the general area designated as numeral 68 comes into contact under significant force with the general area designated as 70 on frame member 20. Bracket member 18 and frame member 20, which are typically constructed of aluminum, create metal-to-metal contact, which during repeated flexion cycles, produces wear in areas 68 and 70, limiting the useful life of the knee component. Consequently by incorporating flexion bumper 58, during knee flexion, ears 38 of the bracket member 18 contact bumper 58 prior to areas 68 and 70 coming into contact. Flexion bumper 58 absorbs the force generated during knee flexion thereby eliminating the destructive results to areas 68 and 70 by coming into contact during flexion. The density of bumper 58 can be adjusted to totally eliminate contact between areas 68 and 70 or reduce the force sufficiently such that when areas 68 and 70 do come into contact, no damage results to the components.

Since areas 68 and 70, without the bumper, contact each other at a location near the center of rotation of the knee component (at main shaft 30), significant stresses are concentrated at the main shaft. By locating the flexion bumper 58 in the upper front corner of the frame member, the area of contact between the bracket member and the frame (at the bumper) is moved away from the center of rotation, thereby reducing the forces on main shaft 30 and the points of bumper contact. The combination of absorbing the forces created during flexion and moving the point of contact farther away from the center of rotation, extends the useful life of the knee component by eliminating the damage to the components themselves, and relieving the stress concentrations at the main shaft. Similarly, by locating the flexion bumper 58 in the upper front corner of brace 20, the total angle of flexion achieved is substantially the same as the knee components without the flexion bumper.

The multi-purpose prosthetic knee component of the present invention has also been designed for the additional purpose of enhancing the performance of runners by incorporating the flexion limiters 64 shown in FIG. 4. Flexion limiters 64 are used optionally and can be left unused unless their function of enhancing running gait is desired. When the flexion limiters are used they are positioned on the frame member below and inwardly from the flexion bumper 58 such that during knee flexion, ears 38 on the bracket member 18 contact the limiters 64 rather than flexion bumper 58. By positioning flexion limiters 64 below and inward from flexion bumper 58, the total angle of flexion is reduced, thereby allowing the frame member to be returned to extension more quickly during use. The performance of a runner or sprinter directly relates to the ability of the knee component to transition quickly from flexion to extension.

Flexion limiters 64 improve, i.e., reduce, the time necessary to transition between flexion and extension by limiting the total angle of flexion. They are made from an elastomeric or rigid material to initially absorb the force generated during flexion and also to provide a springing force to the lower leg to return the lower leg to the extension phase. Suitable elastomeric materials are those materials discussed with respect to flexion bumper 58, however at a density which provides not only force absorption generated during flexion, but also provides inertia to the lower leg in returning to the extension phase. Rigid materials, such as plastic, can be used so long as the durometer hardness is less than the hardness of the bracket member so that damage to the bracket member does not occur when the bracket member and the limiters come into contact. The combination of a shorter flexion angle and providing inertia to return to the extension phase allows the amputee to increase the speed at which a running gait is completed. By bolting the flexion limiters to the inside surface of the frame, they can be easily removed for normal activity.

What is claimed is:

1. A prosthetic knee component for an above-knee prosthesis comprising:
   a frame member;
   a bracket member having means for pivotally connecting the bracket member to the frame member thereby creating a center of rotation for the knee component;
   a force control unit secured between the frame member and the bracket member; and
   a flexion bumper positioned within the frame member b, end plugs, the flexion bumper being sufficiently compressible in a flexion phase of the knee component to provide controlled energy absorbing compliance under force exerted on the bumper by the bracket member.

2. The prosthetic knee component of claim 1 wherein the means for pivotally connecting the bracket member to the frame member comprises a flange extending downwardly on either side of the bracket member and a shaft passing through the flanges and the frame member.

3. The prosthetic knee component of claim 1 wherein said bracket member further includes flanges extending downwardly from a rear portion of the bracket member, said flanges contacting the flexion bumper during said flexion phase and for pivotally connecting the bracket member to the force control unit.

4. The prosthetic knee component of claim 2 wherein the flexion bumper is positioned within the frame member away from the center of rotation of the knee component through axially aligned bores located on each side of the frame member.

5. The prosthetic knee component of claim 4 wherein the end plugs are located in said flanges for applying axial forces to the ends of the bumper for maintaining the bumper within the axially aligned bores.

6. The prosthetic knee component of claim 1 wherein the bracket member is rigidly secured to a thigh component and the frame member is rigidly secured to a lower leg component.

7. The prosthetic knee component of claim 6 wherein the knee component further comprises at least one running gait flexion limiter positioned within an interior surface of the frame member for limiting knee flexion and being sufficiently resilient to provide inertia to the lower leg component during an extension phase.

8. The prosthetic knee component of claim 7 wherein the running gait flexion limiter limits flexion by being positioned downwardly and rearwardly of the flexion bumper.

9. The prosthetic knee component of claim 8 wherein the running gait flexion limiter provides inertia to the lower leg component by being sufficiently resilient in a flexion phase of the knee component to provide a controlled spring rate to the bracket member as the bracket member contacts the running gait flexion limiter to return the lower leg component to an extension phase.

10. An above knee prosthesis comprising:
    a thigh component;
    a lower leg component;
    and a knee component positioned between the thigh component and the lower leg component;
    the knee component having a frame member and a bracket member, the bracket member having means for pivotally connecting the bracket member to the frame member thereby creating a center of rotation for the knee component, a gait control unit secured between the frame member and the bracket member, said bracket member further having attachment means for pivotally connecting the control unit to the bracket member, a flexion bumper compressibly positioned within the frame member by threaded end caps, the flexion bumper being sufficiently compressible in a flexion phase of the knee component to provide controlled energy absorbing compliance under force exerted on the bumper by the bracket member control unit attachment means.

11. The prosthesis of claim 10 wherein the means for pivotally connecting the bracket member to the frame member are flanges extending downwardly from either side of an upper surface of the bracket member and a shaft passing through the flanges and the frame member.

12. The prosthesis of claim 10 wherein the attachment means for pivotally connecting the bracket member to the control unit are flanges extending downwardly from a rear portion of the bracket member.

13. The prosthesis of claim 12 wherein the prosthesis further includes at least one running gait flexion limiter positioned within an interior surface of the frame member for limiting knee flexion and being sufficiently resilient to provide inertia to the lower leg component during an extension phase.

14. The prosthesis of claim 13 wherein the running gait flexion limiter limits flexion by being positioned downwardly and rearwardly the flexion bumper.

15. The prosthesis of claim 14 wherein the flexion limiter provides inertia to the lower leg component by being sufficiently resilient in a flexion phase of the knee component to provide a controlled spring rate to the rear flanges of the bracket member to rapidly return the lower leg component to an extension phase.

16. The prosthesis of claim 10 wherein the flexion bumper is positioned within the frame member away from the center of rotation of the knee component through axially aligned bores located on each side of the frame member.

* * * * *

UNITED STATES PATENT AND TRADEMARK OFFICE
CERTIFICATE OF CORRECTION

PATENT NO. : 5,704,946
DATED : January 6, 1998
INVENTOR(S) : Ted J. Greene

It is certified that error appears in the above-indentified patent and that said Letters Patent is hereby corrected as shown below:

Column 5, line 35, change "member b," to -- member by --.
Column 5, line 50, change "the force" to -- a force --.
Column 6, line 53, after "rearwardly" insert -- of -- .

Signed and Sealed this

Thirtieth Day of November, 1999

Attest:

Q. TODD DICKINSON

Attesting Officer

Acting Commissioner of Patents and Trademarks